United States Patent
Wagner

[11] Patent Number: 6,165,226
[45] Date of Patent: Dec. 26, 2000

[54] ORTHOSIS JOINT

[75] Inventor: Helmut Wagner, Duderstadt, Germany

[73] Assignee: Otto Bock Orthopaedische Industrie Besitz- Und Verwaltungs-Kommanditgesellschaft, Duderstadt, Germany

[21] Appl. No.: 09/297,126

[22] PCT Filed: Jun. 18, 1998

[86] PCT No.: PCT/DE98/01673

§ 371 Date: Apr. 26, 1999

§ 102(e) Date: Apr. 26, 1999

[87] PCT Pub. No.: WO99/11206

PCT Pub. Date: Mar. 11, 1999

[30] Foreign Application Priority Data

Sep. 3, 1997 [DE] Germany .......................... 297 15 794

[51] Int. Cl.[7] ...................................................... A61F 2/62
[52] U.S. Cl. .................................. 623/39; 623/43; 623/46
[58] Field of Search ................................ 623/39, 43, 46

[56] References Cited

U.S. PATENT DOCUMENTS

| | | | |
|---|---|---|---|
| 2,591,373 | 4/1952 | Petruch | 128/80 |
| 4,502,472 | 3/1985 | Pansiera | 128/80 |
| 4,602,472 | 7/1986 | Ampolini et al. | 53/438 |
| 5,460,599 | 10/1995 | Davis et al. | 602/26 |

FOREIGN PATENT DOCUMENTS 0 016 268  10/1980  European Pat. Off. .
269 13 843  12/1996  Germany .

*Primary Examiner*—Dinh X. Nguyen
*Attorney, Agent, or Firm*—Foley & Lardner

[57] ABSTRACT

An orthesis joint, in particular a knee joint for part of a leg, comprising a joint upper part (1) and a joint lower part (2), pivotably connected to the latter by means of a joint screw (3), as well as comprising a manually releasable wedge block (9, 10, 11, 12), the blocking wedge (9) of which, displaceably guided in the joint upper part (1), engages in its blocking position in an approximately radial direction—in relation to the joint screw (3)—into a blocking groove (10), provided on the joint lower part (2), and can be displaced out of this blocking position against the action of a spring (11) into an unlocking position, characterized in that the joint upper part (1) is divided in two in its plane perpendicular to the joint screw (3), into a basic body (4) and a cover (5) covering the latter at least partially, and in that the blocking wedge (9) is guided in mutually corresponding groove-shaped milled recesses (7, 8) in the mutually facing inner sides of the basic body (4) and cover (5).

4 Claims, 4 Drawing Sheets

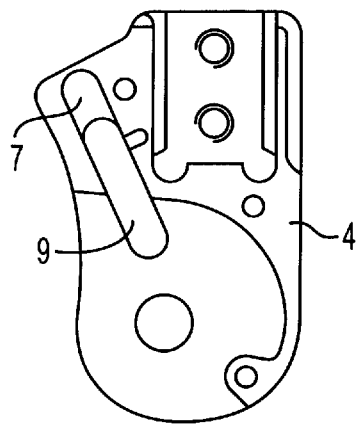
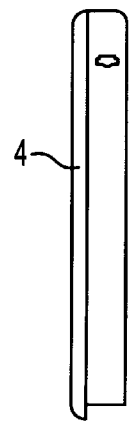
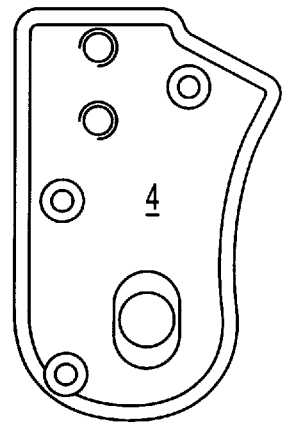
FIG. 6          FIG. 7          FIG. 8
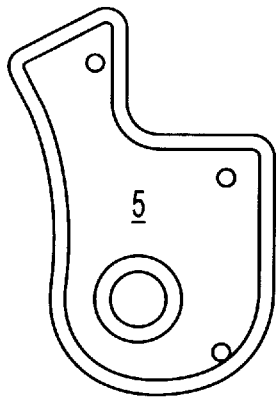
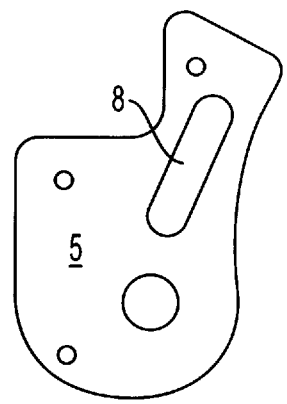
FIG. 9          FIG. 10         FIG. 11

ORTHOSIS JOINT

The invention relates to an orthesis joint, in particular a knee joint for part of a leg, comprising a joint upper part and a joint lower part, pivotably connected to the latter by means of a joint screw, as well as comprising a manually releasable wedge block, the blocking wedge of which, displaceably guided in the joint upper part, engages in its blocking position in an approximately radial direction—in relation to the joint screw—into a blocking groove, provided on the joint lower part, and can be displaced out of this blocking position against the action of a spring into an unlocking position.

In a known embodiment, the guide for the blocking wedge is of an open form in an integrally designed joint upper part. The actuation of the blocking wedge takes place by means of a blocking rocker, which is articulated on the joint upper part, reaches over the latter on both sides and on the free end of which there acts a pulling member to be manually activated. By pulling up the blocking rocker, the blocking wedge held between the two legs of said rocker is raised upward out of its locking position.

The invention is based on the object of improving the functionality of the orthesis joint described at the beginning.

This object is achieved according to the invention by the joint upper part being divided in two in its plane perpendicular to the joint screw, into a basic body and a cover covering the latter at least partially, and by the blocking wedge being guided in mutually corresponding groove-shaped milled recesses in the mutually facing inner sides of the basic body and cover.

Consequently, according to the invention, an encapsulated guide is provided for the blocking wedge. This has the effect of preventing soiling in the displacing region of the blocking wedge and of thereby improving the functionality. The milled recesses reaching over the blocking wedge on both sides form a very exact guide and therefore allow a reliable, canting-free displacement of the blocking wedge. The encapsulated embodiment, also covering the compression spring, leads to a more pleasing appearance of the construction, which is of great significance in the case of the usually to be openly worn ortheses.

An activation of the wedge block that is particularly favorable with regard to the exertion of force is ensured if a pulling element to be manually activated, preferably a Perlon cord, acts directly on the blocking wedge in its direction of displacement.

A joint connection that is particularly stable and largely protected against soiling can be achieved according to the invention by the joint lower part being pivotably guided with a portion of a disk-shaped design, receiving the joint screw and having at least one blocking groove, in a sandwich-like manner between the basic body and the cover of the joint upper part.

Further advantages emerge from the representation and explanation of an exemplary embodiment.

An embodiment of the invention serving as an example is represented in the drawing, in which:

FIG. 6 shows the inside of a basic body forming the joint upper part;

FIG. 7 shows the basic body according to FIG. 6 in an end view;

FIG. 8 shows the rear side of the basic body according to FIG. 6;

FIG. 9 shows the inner side of a cover covering the basic body according to FIGS. 6 to 8;

FIG. 10 shows the cover according to FIG. 9 in an end view, and

FIG. 11 shows the rear side of the cover according to FIG. 9.

Figure 1:
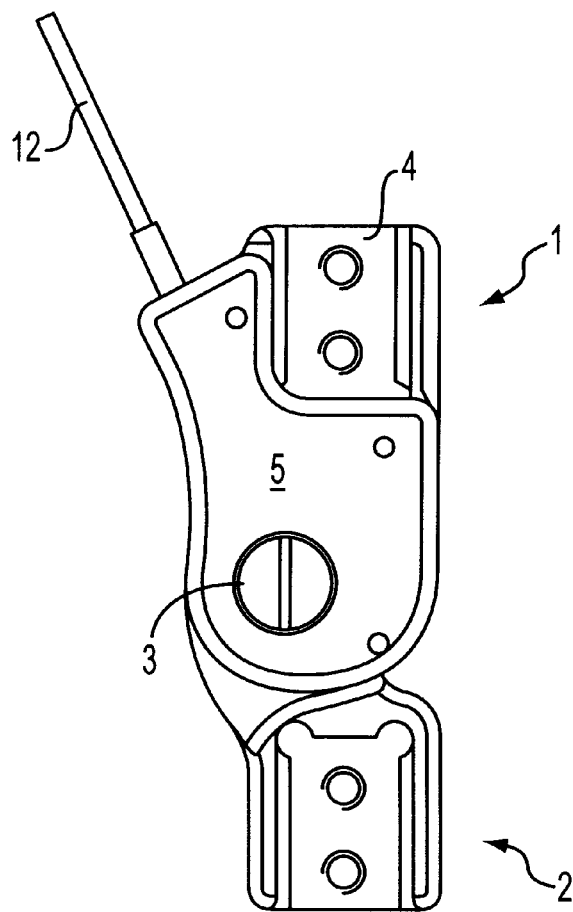
FIG. 1 shows an orthesis knee joint in an outer side view.
Figure 2:
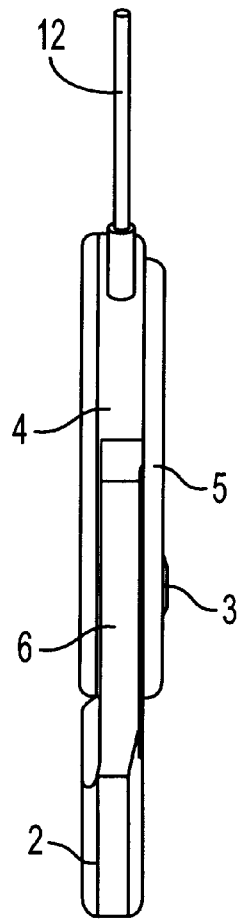
FIG. 2 shows the representation according to FIG. 1 in an end view.
Figure 3:
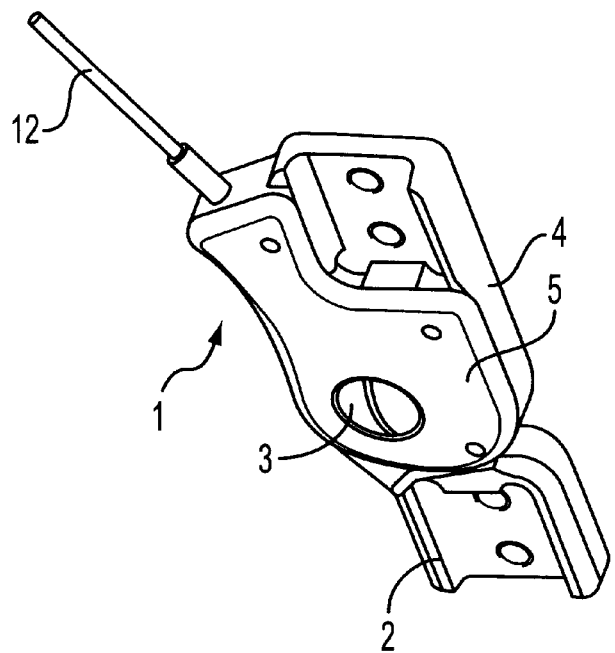
FIG. 3 shows the embodiment according to FIG. 1 in a perspective representation.
Figure 4:
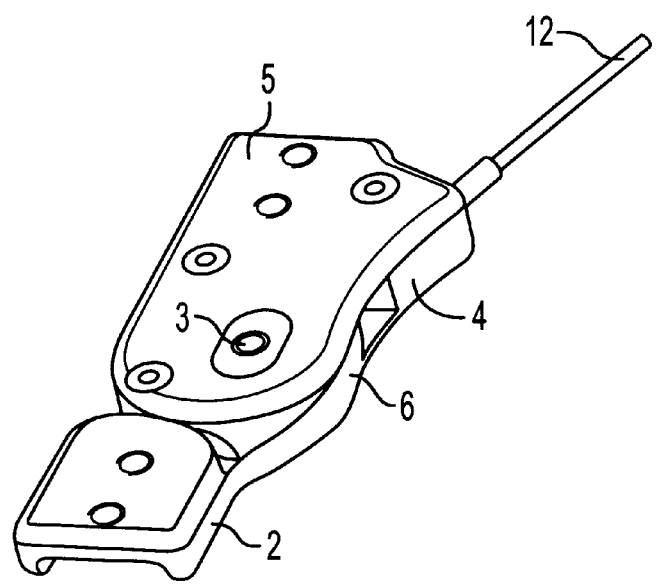
FIG. 4 shows the representation according to FIG. 3 in a rear view.
Figure 5:
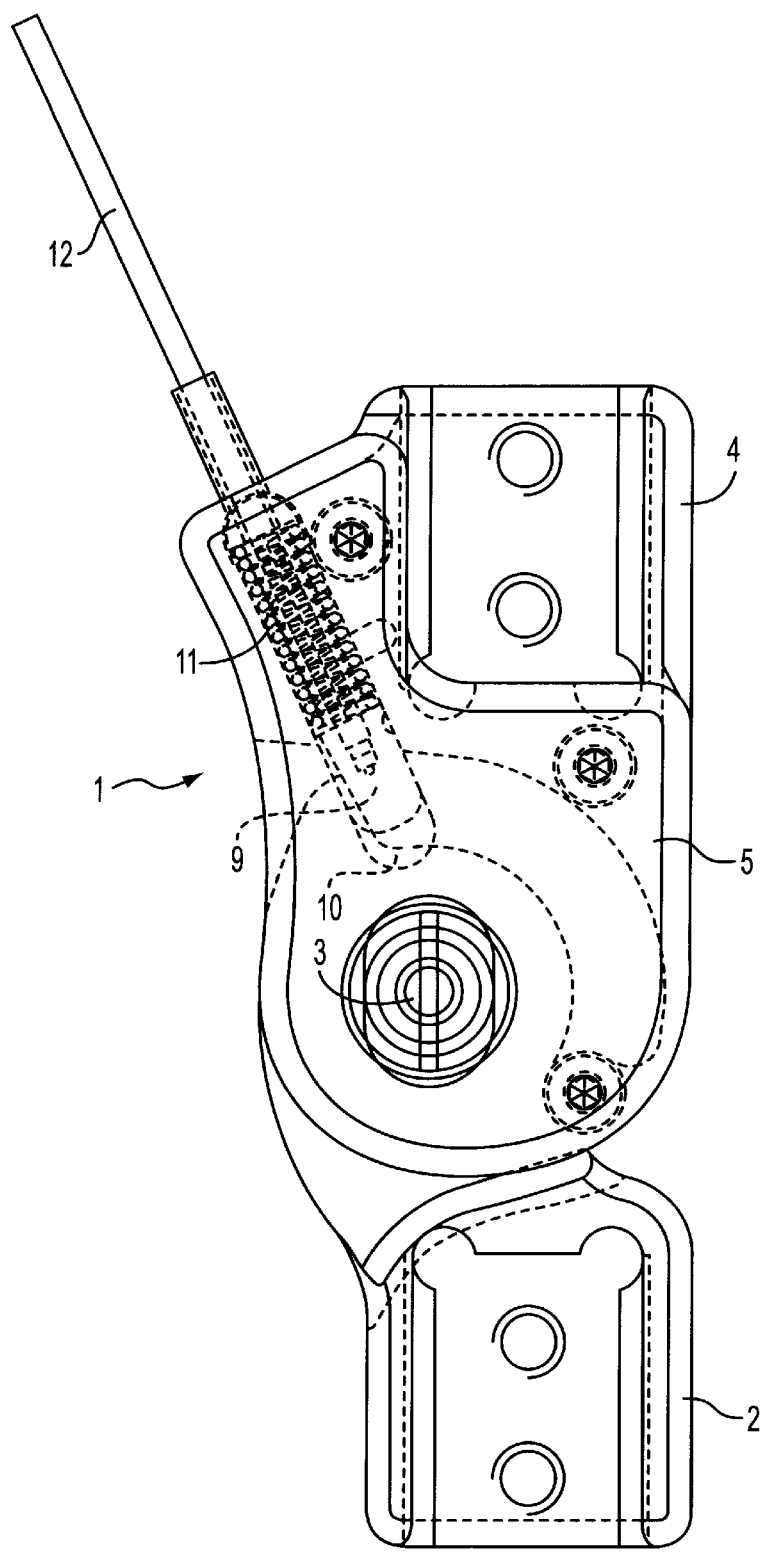
FIG. 5 shows the representation according to FIG. 1 on an enlarged scale, with the wedge block depicted by dashed lines.

FIGS. 1 to 5 shows an orthesis joint, which is designed as a knee joint for part of a leg. This knee joint substantially comprises a joint upper part 1 and a joint lower part 2, which are pivotably connected to each other by means of a joint screw 3.

The joint upper part 1 is divided in two in its plane perpendicular to the joint screw 3, into a basic body 4 and a cover 5 covering the latter at least partially. In the assembled state, a portion 6 of the joint lower part 2 of a disk-shaped design and receiving the joint screw 3 is pivotably guided in a sandwich-like manner between the basic body 4 and the cover 5.

Provided in the inner side of the basic body 4 and in the inner side of the cover 5 there is in each case a groove-shaped milled recess 7, 8, which in the assembled state receive a displaceable blocking wedge 9 between them. This blocking wedge 9 engages in its blocking position in an approximately radial direction—in relation to the joint screw 3—into a blocking groove 10, which is provided on the upper outer edge of the portion 6 of the joint lower part 2, and can be displaced out of this blocking position against the action of a compression spring 11 into an unlocking position. This unlocking takes place by manual activation, to be precise by pulling on a Perlon cord 12, which acts directly on the blocking wedge 9 in the direction of displacement of the latter, that is to say in the direction of the elongate milled recesses 7, 8.

What is claimed is:

1. Orthesis joint, in particular a knee joint for part of a leg, comprising a joint upper part (1) and a joint lower part (2), pivotably connected to the latter by means of a joint screw (3), as well as comprising a manually releasable wedge block (9, 10, 11, 12), the blocking wedge (9) of which, displaceably guided in the joint upper part (1), engages in its blocking position in an approximately radial direction—in relation to the joint screw (3)—into a blocking groove (10), provided on the joint lower part (2), and can be displaced out of this blocking position against the action of a spring (11) into an unlocking position, characterized in that the joint upper part (1) is divided in two in its plane perpendicular to the joint screw (3), into a basic body (4) and a cover (5) covering the latter at least partially, and in that the blocking wedge (9) is guided in mutually corresponding groove-shaped milled recesses (7, 8) in the mutually facing inner sides of the basic body (4) and cover (5).

2. Orthesis joint as claimed in claim 1, characterized in that a pulling element to be manually activated, preferably a Perlon cord (12), acts directly on the blocking wedge (9) in its direction of displacement.

3. Orthesis joint as claimed in claim 1, characterized in that the joint lower part (2) is pivotably guided with a portion (6) of a disk-shaped design, receiving the joint screw (3) and having at least one blocking groove (19), in a sandwich-like manner between the basic body (4) and the cover (5) of the joint upper part (1).

4. Orthesis joint as claimed in claim 2, characterized in that the joint lower part (2) is pivotably guided with a portion (6) of a disk-shaped design, receiving the joint screw (3) and having at least one blocking groove (19), in a sandwich-like manner between the basic body (4) and the cover (5) of the joint upper part (1).

* * * * *